United States Patent [19]

Smith

[11] 4,156,088

[45] May 22, 1979

[54] ω-ARYL-13,14-DIDEHYDRO-INTERPHENY-LENE-PGA COMPOUNDS

[75] Inventor: Herman W. Smith, Kalamazoo, Mich.

[73] Assignee: The Upjohn Company, Kalamazoo, Mich.

[21] Appl. No.: 901,059

[22] Filed: Apr. 28, 1978

Related U.S. Application Data

[62] Division of Ser. No. 776,552, Mar. 7, 1977, which is a division of Ser. No. 657,739, Feb. 13, 1976, Pat. No. 4,029,681.

[51] Int. Cl.$^2$ ............................................. C07C 177/00
[52] U.S. Cl. ....................................... 560/53; 562/463
[58] Field of Search .............. 560/53, 520 R; 562/463

*Primary Examiner*—Paul J. Killos
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

36 Claims, No Drawings

ω-ARYL-13,14-DIDEHYDRO-INTERPHENYLENE-PGA COMPOUNDS

The present application is a divisional application of Ser. No. 776,552, filed Mar. 7, 1977; which is a divisional application of Ser. No. 657,739, filed Feb. 13, 1976, issued as U.S. Pat. No. 4,029,681 on June 14, 1977.

The present invention relates to prostaglandin analogs, for which the essential material constituting disclosure therefor is incorporated by reference here from Ser. No. 657,739, filed Feb. 13, 1976, now issued as U.S. Pat. No. 4,029,681.

I claim:

1. A prostaglandin analog of the formula:

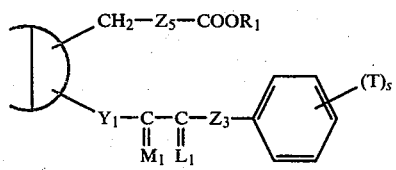

wherein D is

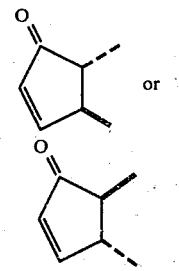

wherein $Y_1$ is —C≡C—;
wherein $Z_5$ is

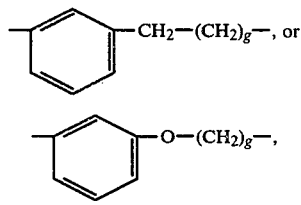

wherein g is one, 2, or 3;
wherein $Z_3$ is oxa or methylene;
wherein T is chloro, fluoro, trifluoromethyl, alkyl of one to 3 carbon atoms, inclusive, or alkoxy of one to 3 carbon atoms, inclusive, and s is zero, one, 2, or 3, the various T's being the same or different, with the proviso that not more than two T's are other than alkyl;
wherein $M_1$ is

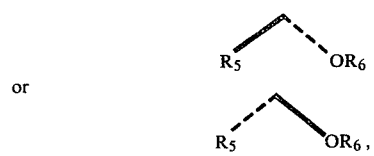

wherein $R_5$ and $R_6$ are hydrogen or methyl, with the proviso that one of $R_5$ and $R_6$ is methyl only when the other is hydrogen;
wherein $L_1$ is

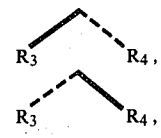

or a mixture of

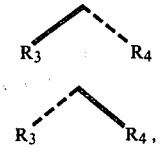

wherein $R_3$ and $R_4$ are hydrogen, methyl, or fluoro, being the same or different, with the proviso that one of $R_3$ and $R_4$ is fluoro only when the other is hydrogen or fluoro and $Z_3$ is methylene; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1 wherein D is

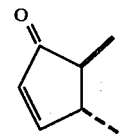

3. A compound according to claim 1 wherein D is

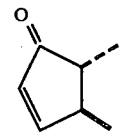

4. A compound according to claim 3 wherein $Z_3$ is methylene.

5. A compound according to claim 4 wherein s is zero or one and T is chloro, fluoro, or trifluoromethyl.

6. A compound according to claim 3 wherein $Z_3$ is oxa.

7. A compound according to claim 6 wherein s is zero.

8. A compound according to claim 6 wherein s is zero or one and T is chloro, fluoro, or trifluoromethyl.

9. A compound according to claim 8 wherein $Z_1$ is

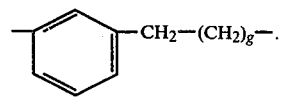

10. A compound according to claim 8 wherein $Z_1$ is

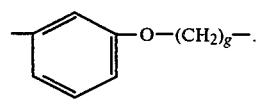

11. A compound according to claim 8 wherein $M_1$ is

12. A compound according to claim 11 wherein g is one.

13. A compound according to claim 12 wherein $R_3$, $R_4$, $R_5$, and $R_6$ are all hydrogen.

14. 15-epi-3,7-Inter-m-phenylene-3-oxa-4,5,6,17,18,19,20-heptanor-13,14-didehydro-PGA$_1$, methyl ester, a compound according to claim 13.

15. A compound according to claim 13, wherein $M_1$ is

16. A compound according to claim 15, wherein g is three.

17. A compound according to claim 15, wherein g is one.

18. A compound according to claim 17, wherein $R_3$ and $R_4$ are both hydrogen.

19. A compound according to claim 18 wherein $R_5$ is methyl.

20. 3,7-Inter-m-phenylene-3-oxa-4,5,6,17,18,19,20-heptanor-16-phenoxy-15-methyl-13,14-didehydro-PGA$_1$, a compound according to claim 19.

21. 3,7-Inter-m-phenylene-3-oxa-4,5,6,17,18,19,20-heptanor-16-phenoxy-15-methyl-13,14-didehydro-PGA$_1$, methyl ester, a compound according to claim 19.

22. A compound according to claim 18 wherein $R_6$ is methyl.

23. 3,7-Inter-m-phenylene-3-oxa-4,5,6,17,18,19,20-heptanor-16-phenoxy-13,14-didehydro-PGA$_1$, 15-methyl ether, a compound according to claim 22.

24. 3,7-Inter-m-phenylene-3-oxa-4,5,6,17,18,19,20-heptanor-16-phenoxy-13,14-didehydro-PGA$_1$, methyl ester, 15-methyl ether, a compound according to claim 22.

25. A compound according to claim 18, wherein $R_5$ and $R_6$ are both hydrogen.

26. 3,7-Inter-m-phenylene-3-oxa-4,5,6,17,18,19,20-heptanor-16-phenoxy-13,14-didehydro-PGA$_1$, a compound according to claim 25.

27. 3,7-Inter-m-phenylene-3-oxa-4,5,6,17,18,19,20-heptanor-16-phenoxy-13,14-didehydro-PGA$_1$, methyl ester, a compound according to claim 25.

28. A compound according to claim 17, wherein at least one of $R_3$ and $R_4$ is methyl.

29. A compound according to claim 28, wherein $R_3$ and $R_4$ are both methyl.

30. A compound according to claim 29, wherein $R_5$ is methyl.

31. 3,7-Inter-m-phenylene-3-oxa-4,5,6,18,19,20-hexanor-16-phenoxy-15,16-dimethyl-13,14-didehydro-PGA$_1$, methyl ester, a compound according to claim 30.

32. A compound according to claim 29, wherein $R_6$ is methyl.

33. 3,7-Inter-m-phenylene-3-oxa-4,5,6,18,19,20-hexanor-16-phenoxy-16-methyl-13,14-didehydro-PGA$_1$, methyl ester, 15-methyl ether, a compound according to claim 32.

34. A compound according to claim 29, wherein $R_5$ and $R_6$ are both hydrogen.

35. 3,7-Inter-m-phenylene-3-oxa-4,5,6,18,19,20-hexanor-16-phenoxy-16-methyl-13,14-didehydro-PGA$_1$, a compound according to claim 34.

36. 3,7-Inter-m-phenylene-3-oxa-4,5,6,18,19,20-hexanor-16-phenoxy-16-methyl-13,14-didehydro-PGA$_1$, methyl ester, a compound according to claim 34.

* * * * *

UNITED STATES PATENT OFFICE
CERTIFICATE OF CORRECTION

Patent No. 4,156,088     Dated  22 May 1979

Inventor(s)  Herman W. Smith

It is certified that error appears in the above-identified patent and that said Letters Patent are hereby corrected as shown below:

Patent should include the following
-- References Cited
U.S. PATENT DOCUMENTS
3,933,898  1/1976  Nelson, N.A.  560/53
3,933,895  1/1976  Nelson, N.A.  560/53 --

Column 3, line 12, "heptanor-13,14-didehydro-" should read -- heptanor-16-phenoxy-13,14-didehydro- --.

Signed and Sealed this

Eleventh Day of November 1980

[SEAL]

Attest:

SIDNEY A. DIAMOND

Attesting Officer     Commissioner of Patents and Trademarks

UNITED STATES PATENT AND TRADEMARK OFFICE
CERTIFICATE OF CORRECTION

PATENT NO. : 4,156,088

DATED : May 22, 1979

INVENTOR(S) : Herman W. Smith

It is certified that error appears in the above—identified patent and that said Letters Patent is hereby corrected as shown below:

```
Patent should include the following
-- References Cited
U.S. PATENT DOCUMENTS
3,933,898  1/1976  Nelson, N.A.  560/53
3,933,895  1/1976  Nelson, N.A.  560/53 --
```

Column 3, line 12, "heptanor-13,14-didehydro-" should read -- heptanor-16-phenoxy-13,14-didehydro- --.

Signed and Sealed this

Nineteenth Day of May 1981

[SEAL]

Attest:

Attesting Officer

RENE D. TEGTMEYER

Acting Commissioner of Patents and Trademarks